United States Patent [19]

Vauchier et al.

[11] Patent Number: 4,795,579

[45] Date of Patent: Jan. 3, 1989

[54] 2,2'-DIFLUORO-4-ALKOXY-4'-HYDROXYDIPHENYLS AND THEIR DERIVATIVES, THEIR PRODUCTION PROCESS AND THEIR USE IN LIQUID CRYSTAL DISPLAY DEVICES

[75] Inventors: Claude Vauchier, Goncelin; Françoise Vinet, Grenoble, both of France

[73] Assignee: Commissariat a l'Energie Atomique, Paris, France

[21] Appl. No.: 19,058

[22] Filed: Feb. 26, 1987

[30] Foreign Application Priority Data

Feb. 28, 1986 [FR]  France ................................ 86 02858

[51] Int. Cl.$^4$ .......................... G02F 1/13; C09K 19/32; C09K 19/30; C09K 19/12; C07C 69/74; C07C 69/76

[52] U.S. Cl. ........................... 252/299.62; 252/299.01; 252/299.5; 252/299.63; 252/299.65; 252/299.66; 350/350 R; 350/350 S; 558/270; 560/1; 560/73; 560/108; 560/114; 560/116; 560/118; 560/126; 560/141

[58] Field of Search ...................... 558/270; 560/1, 73, 560/108, 116, 118, 126, 141; 252/299.62, 299.63, 299.65, 299.66, 299.5, 299.01; 350/350 R, 350 S

[56] References Cited

U.S. PATENT DOCUMENTS

| | | | |
|---|---|---|---|
| 3,947,375 | 3/1976 | Gray et al. | 252/299.66 |
| 4,029,594 | 6/1977 | Gavrilovic et al. | 252/299.65 |
| 4,073,742 | 2/1978 | Erdmann et al. | 252/299.65 |
| 4,216,109 | 8/1980 | Mizukuchi | 252/299.65 |
| 4,368,135 | 1/1983 | Osman | 252/299.63 |
| 4,400,293 | 8/1983 | Romer et al. | 252/299.63 |
| 4,415,470 | 11/1983 | Eidenschink et al. | 252/299.63 |
| 4,419,264 | 12/1983 | Eidenschink et al. | 252/299.63 |
| 4,490,305 | 12/1984 | Eidenschink et al. | 252/299.63 |
| 4,542,230 | 9/1985 | Gray et al. | 252/299.63 |
| 4,594,465 | 6/1986 | Chan et al. | 252/299.66 |
| 4,602,851 | 7/1986 | Jenner et al. | 252/299.63 |
| 4,695,131 | 9/1987 | Balkwill et al. | 252/299.63 |
| 4,696,549 | 9/1987 | Chan et al. | 252/299.63 |
| 4,737,313 | 4/1988 | Saito et al. | 252/299.63 |

FOREIGN PATENT DOCUMENTS

| | | | |
|---|---|---|---|
| 23728 | 2/1981 | European Pat. Off. | 252/299.63 |
| 84194 | 7/1983 | European Pat. Off. | 252/299.61 |
| 0153826 | 9/1985 | European Pat. Off. | 252/299.63 |
| 2939782 | 4/1981 | Fed. Rep. of Germany | 252/299.65 |
| 59-76029 | 4/1984 | Japan | 252/299.67 |
| 2071649 | 9/1981 | United Kingdom | 252/299.62 |
| 2098987 | 12/1982 | United Kingdom | 252/299.67 |

Primary Examiner—Teddy S. Gron
Attorney, Agent, or Firm—Pearne, Gordon, McCoy & Granger

[57] ABSTRACT

The invention relates to novel compounds usable as liquid crystals in liquid crystal display devices utilizing the electrically controlled birefringence effect.

These compounds comply with formula:

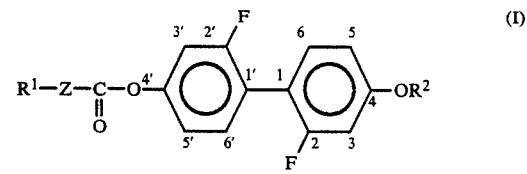

in which $R^1$ represents an alkoxy or alkyl radical with 1 to 12 carbon atoms and Z represents a single bond or a radical chosen from among:

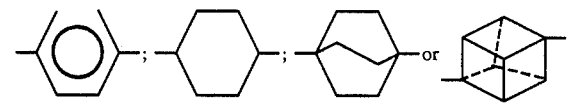

provided that $R^1$ represents an alkyl radical when Z represents a single bond and $R^2$ represents an alkyl radical with 1 to 12 carbon atoms.

They can be obtained by reacting an acid chloride of formula $R^1$—z—COCL with a 2,2'-difluoro-4-alkoxy-4'-hydroxydiphenyl of formula:

(Abstract continued on next page.)

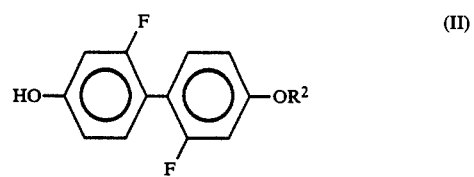
(II)
8 Claims, 1 Drawing Sheet

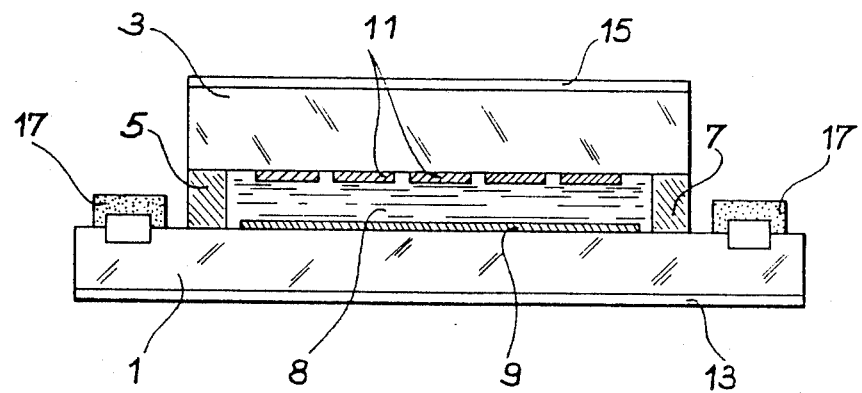

2,2'-DIFLUORO-4-ALKOXY-4'-HYDROXYDIPHENYLS AND THEIR DERIVATIVES, THEIR PRODUCTION PROCESS AND THEIR USE IN LIQUID CRYSTAL DISPLAY DEVICES

BACKGROUND OF THE INVENTION

The present invention relates to the synthesis of novel liquid crystals, more particularly usable in liquid crystal display devices utilizing the electrically controlled birefringence effect. This effect corresponds to a deformation under an electric field of a nematic phase with negative dielectric anisotropy $\Delta\epsilon$, $\Delta\epsilon$ representing the difference between the dielectric constant $\epsilon_a$ parallel to the major molecular axis of the crystal and the dielectric constant $\epsilon_b$ perpendicular to said major axis.

In liquid crystal display devices, it is necessary to use materials having a high multiplexing rate, i.e. giving the possibility of electrically addressing a large number of rows of the screen, in order to display a high information rate. This multiplexing rate k can be expressed as a function of the voltage applied to the terminals of the device (V) and the threshold deformation voltage of the crystal ($V_S$) by the formula:

$$k < \left(\frac{V^2 + V_S^2}{V^2 - V_S^2}\right)^2$$

For a given multiplexing rate, it is necessary to have a molecular tilt angle ($\phi_M$) at the centre of the liquid crystal cell which is as large as possible, in order to obtain an optimum contrast between the two black and white states of the crystal under the action of the electric field. For small tilt angles $\phi_M$ is directly linked with the threshold deformation voltage of the crystal $V_S$ and with respect to the flexion $K_{33}$ and fanning $K_{11}$ elastic constants of the liquid crystal. Thus, $\phi_M$ is given by the formula:

$$\phi_M = \frac{V^2 - V_S^2}{V^2\epsilon\frac{2}{3} + \left|\frac{\Delta\epsilon}{\epsilon_a}\right| - \eta_{31}V_S^2}$$

$$\text{with } V_S = 2n\sqrt{\frac{nK_{33}}{\Delta\epsilon}}$$

$$\Delta\epsilon = \epsilon_a - \epsilon_b \ldots$$

$$\eta_{31} = \frac{1 - K_{33}}{K_{11}}$$

Under these conditions, the electrically induced birefringence is of the form:

$$\Delta n = \left(\frac{\sin^2\phi}{n_o^2} + \frac{\cos^2\phi}{n_e^2}\right)^{\frac{1}{2}} - n_0$$

$$\text{with } \phi \approx \phi_M \cos\frac{\pi}{e} Z$$

in which $n_e$ and $n_o$ are the extraordinary and ordinary indices of the crystal, e the liquid crystal thickness and Z its position in the cell.

The relative intensity transmitted by the liquid crystal device between two crossed polarizers is given by the relation:

$$\frac{I}{I_0} = \sin^2 \pi \frac{\Delta n \, e}{\lambda}$$

in which $\Delta n$ is equal to $n_e - n_o$ and $\lambda$ is the wavelength of the light beam illuminating the device. Therefore the most important parameters of the material are $K_{33}/K_{11}$, $\Delta n$, $\Delta\epsilon$ and the mesomorphism range $\Delta T$ of the crystal.

The ratio $K_{33}/K_{11}$ plays an important part among these parameters, because it determines the steepness of the slope of the electrooptical transfer curve and therefore the multiplexibility of the material used and said ratio must be as large as possible.

As a function of the nematic compounds used, this ratio can vary from 0.5 to 3, the most widely used value being approximately 1. In order to have a higher value of the ratio $K_{33}/K_{11}$, consideration can be given to increasing the value of $K_{33}$ or decreasing the value of $K_{11}$.

A high value of $K_{33}$ is of no interest in display devices, because it involves the use of high control voltages. Thus, the threshold deformation voltage of the crystal $V_s$ is proportional to the value of the elastic deformation constant in flexion $K_{33}$ according to the formula:

$$V_s = 2\pi\sqrt{\frac{\pi R_{33}}{|\Delta\epsilon|}}$$

It is therefore preferable to reduce the value of $K_{11}$, which corresponds to decreasing the intermolecular interactions between the molecules of the liquid crystal. Generally, the nematic liquid crystal molecules are formed by a rigid central part having phenyl groups and one or more flexible parts located at the ends of the rigid part.

Several solutions have been considered for reducing the interactions between molecules of this type. One of the solutions is to replace a phenyl cycle of the rigid part by a cyclohexane or a bicyclo-octane nucleus. Thus, as a result of the substantially globular shape of the latter nucleus and as a result of its completely saturated bonds, it does not favour intermolecular interactions and this makes it possible to minimize the value of $K_{11}$ and increase the $K_{33}/K_{11}$ ratio. A second solution is to substitute one or more hydrogen atoms of the phenyl nucleus by an electro-negative element, such as fluorine.

Recently, novel liquid crystals have been synthesized for which the $K_{33}/K_{11}$ ratio has a high value. These novel liquid crystals are e.g.:

alkylfluorophenyl-alkylbicyclo(2,2,2)-octane carboxylates, like compound BCO55F complying with the following formula:

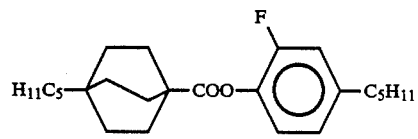

4-(trans-4-n alkylcyclohexyl)-4'-alkyl-2,2' difluorodiphenyls, such as compound BCH52FF of formula:

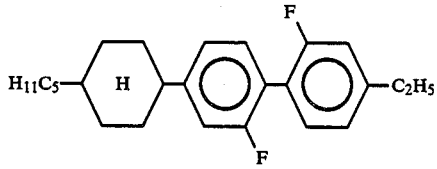

and bicyclohexylcarbonitriledialkyls or alkylalkylenes.

Such compounds have the following characteristics:

| COMPOUND | $K_{33}/K_{11}$ | n | $\Delta\epsilon$ |
|---|---|---|---|
|  | 1. | 0.13 | −1 |
| BC055F | 1.35 | 0.06 | −0.75 |
| BCH52FF | 1.7 | 0.99 | −0.47 |

As can be seen from the above table the first line gives the characteristics required for display devices using electrically controlled birefringence, said compounds only being advantageous from the elastic constant standpoint, the value of the $K_{33}/K_{11}$ ratio being high. However, their other characteristics (n and $\Delta\epsilon$) do not make it possible to obtain the requisite electrooptical properties for display devics. Therefore consideration has been given to the use of these compounds mixed with other liquid crystals for improving the electrooptical properties, but this leads to a significant drop in the value of the $K_{33}/K_{11}$ ratio.

SUMMARY OF THE INVENTION

The present invention relates to novel compounds usable as liquid crystals, which have a number of electrooptical parameters better satisfying the conditions required for use in liquid crystal display devices using the electrically controlled birefringence effect.

These compounds are 2,2'-difluoro-4-alkoxy-4'-hydroxy diphenyl derivatives in accordance with formula:

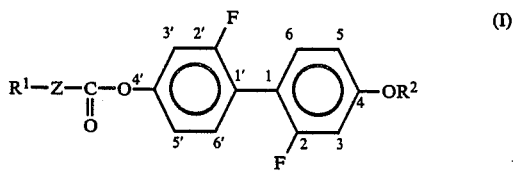

(I)

in which $R^1$ represents a straight or branched alkoxy or alkyl radical with 1 to 12 carbon atoms, Z represents a single bond or a radical chosen from among:

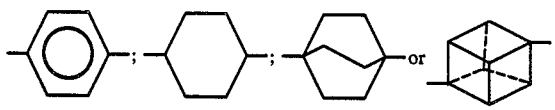

provided that $R^1$ represents an alkyl radical when Z represents a single bond and $R^2$ represents a straight or branched alkyl radical with 1 to 12 carbon atoms.

The compounds defined hereinbefore have a structure making it possible to obtain high values of the $K_{33}/K_{11}$ ratio. Thus, these molecules are long and rigid, so that it is difficult to obtain flexion deformations under the action of an electric field. Thus, the value of $K_{33}$ is high. Moreover, the presence of fluorine atoms in the 2 and 2' position on the diphenyl leads to a twisting of the two phenyl nuclei with respect to one another. The two most favourable positions correspond to torsion angles equal to 30° and 120°. Thus, the molecule is no longer planar and the compact stack of molecules is not assisted as much as in the case of planar molecules. Therefore the intermolecular interactions are weakened and the value of the fanning constant $K_{11}$ of the compound decreases. This is accentuated on passing from Z representing a single bond to Z representing a radical and it increases in the following sense: phenylene, cyclohexylene, bicyclooctylene or radical derived from cubanite.

Examples of compounds according to formula (I) of the invention are:

2,2'-difluoro-4-alkoxy-4'-hydroxydiphenyl of formula:

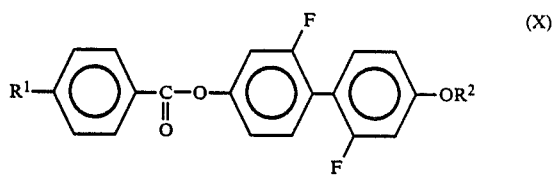

(X)

in which $R^1$ is the butyloxy radical and $R^2$ the ethyl radical or in which $R^1$ is the decyloxy radical and $R^3$ is the 2-methylbutyl radical (S);

2,2'-difluoro-4-alkoxy-4'-hydroxydiphenyl derivatives of formula:

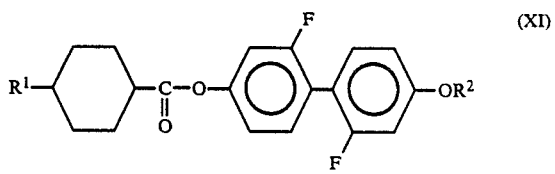

(XI)

in which $R^1$ is an alkyl radical with 3 to 5 carbon atoms and in which $R^2$ is an alkyl radical with 2 to 5 carbon atoms;

2,2'-difluoro-4-alkoxy-4'-hydroxydiphenyl derivatives of formula:

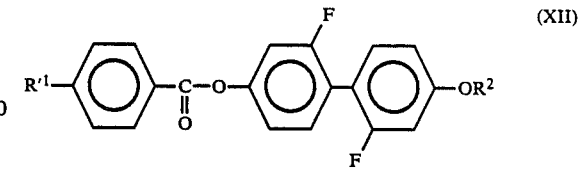

(XII)

in which $R^1$ is an alkyl radical with 6 to 8 carbon atoms and $R^2$ an alkyl radical with 2 to 5 carbon atoms; and the 2,2'-difluoro-4-alkoxy-4'-hydroxydiphenyl derivative of formula:

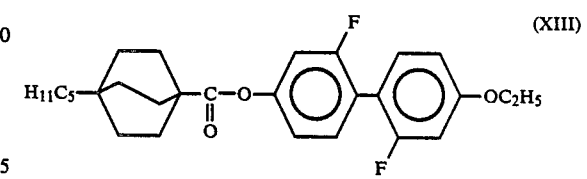

(XIII)

The above-described 2,2'-difluoro-4-alkoxy-4'-hydroxydiphenyl derivatives also have interesting properties as regards to the mesomorphism interval ΔT of the liquid crystal and the electrooptical parameters Δn and Δε.

These compounds can also be used for producing screens of liquid crystal display devices using the electrically controlled birefringence effect. In this case, use is made of at least one compound according to the invention for forming the screen. It is possible to use a single compound or a mixture of several compounds in accordance with formula (I) of the invention. In particular, the use of a mixture makes it possible to obtain appropriate characteristics, e.g. widening the mesomorphism interval toward temperatures below ambient temperature.

It is also possible to use one or more compounds of formula (I) of the invention in association with other liquid crystals for forming a liquid crystal composition constituting the best compromise between all the parameters such as the ratio of the elastic constants, the mesomorphism interval or range, etc.

The invention also relates to a mixture of liquid crystals comprising at least one compound of formula (I) and at least one compound chosen from among:

(a) the Schiff bases according to formula:

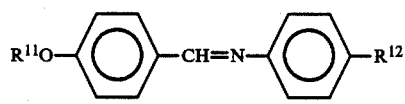

in which $R^{11}$ and $R^{12}$, which can be the same or different, are alkyl radicals with 1 to 7 carbon atoms;

(b) 1-(alkylcyclohexyl)-2-(alkylfluorodiphenylyl)-ethane of formula:

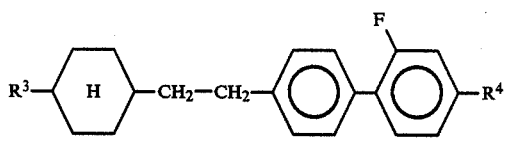

in which $R^3$ and $R^4$ which can be the same or different, are alkyl derivatives with 1 to 7 carbon atoms and (c) alkylfluorophenyl-alkylbicyclooctane carboxylates of formula:

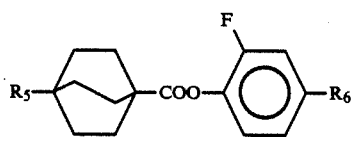

in which $R_5$ and $R_6$, which can be the same or different, are alkyl radicals with 1 to 7 carbon atoms, (d) cyclohexyldiphenyls of formula:

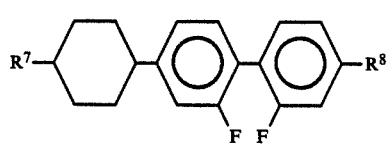

in which $R_7$ is an alkyl radical with 1 to 12 carbon atoms and $R_8$ is an alkyl or alkoxy radical with 1 to 12 carbon atoms.

In these mixtures, the minimum content of compound or compounds of formula (I) is preferably at least 10% by weight and generally at least 20% by weight.

As a result of the association of at least one compound of formula (I) with one or more compounds chosen from among (a), (b), (c) and (d) referred to hereinbefore, a liquid crystal composition is obtained constituting the best compromise between all the parameters:- ratio of the elastic constants $K_{33}/K_{11} \geq 1.3$, wide mesomorphism range, lower viscosity, better homeotropic orientation in the crystals.

The different constituents of the mixture are mostly known products and can be prepared by conventional processes.

Thus, the 1-(alkylcyclohexyl)-2-(alkylfluorodiphenylyl)ethanes of formula (XV) can be prepared by using the method described in British Pat. No. 2 133 795.

Examples of compounds of this type which can be used in the invention are 1-(trans-4-n-ethylcyclohexyl)-2-[2'-fluoro-4'-(2-ethyl)-4-diphenylyl]-ethane (I22) of formula:

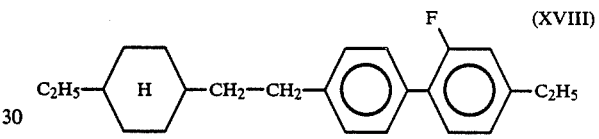

1-(trans-4-n-propylcyclohexyl)-2-[2'fluoro-4'-(2-pantyl)-4-diphenylyl]-ethane (I35) of formula:

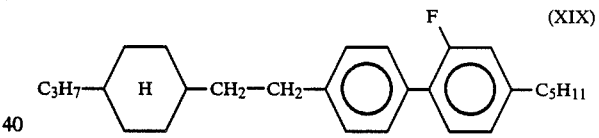

1-(trans-4-n-propylcyclohexyl)-2-[2'-fluoro-4'-(2-ethyl)-4-diphenylyl]-ethane (I32) of formula:

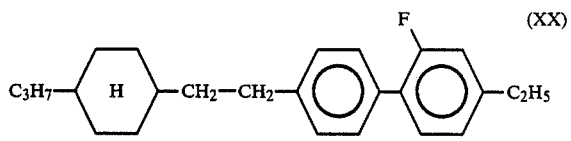

1-(trans-4-n-pentylcyclohexyl)-2-[2'-fluoro-4'-(2-ethyl)-4-diphenylyl]-ethane (I52) of formula:

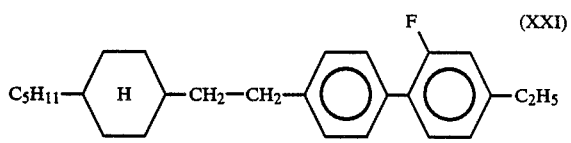

The alkylfluorophenyl-alkylbicyclooctane carboxylates of formula (XVI) can be prepared by the method described by G. W. Gray and S. M. Kelly in Mol. Cryst. Liq. Cryst., 1981, vol.75, pp.109–119.

Examples of compounds of this type which can be used are 2-fluoro-4-n-pentyl-phenyl-4-n-pentyl-bicyclooctane carboxylate (BCO55F) of formula:

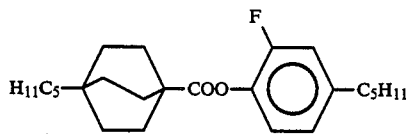
(XXII)

and 2-fluoro-4-n-heptylphenyl-4-n-pentyl-bicyclooctane carboxylate (BCO57F) of formula:

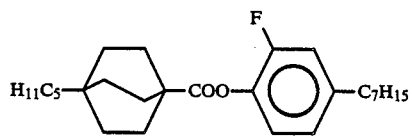
(XXIII)

The cyclohexyldiphenyls of formula (XVII) can be prepared by procedures described in U.S. Pat. No. 4,415,470. An example of such compounds is the cyclohexyldiphenyl of formula:

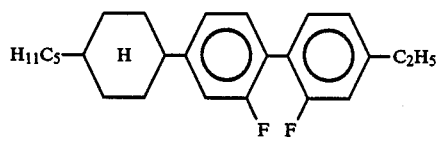
(XXIV)

which will hereinafter be called BCH52FF.

The Schiff bases can be prepared by using the method described by H. Kelker and B. Scheuble in Angew. Chem. Internat. Ed., vol.8, 1969, no.11, pp.884–885. An example of the Schiff bases which can be used in the invention is p-butylaniline-p-methoxybenzylidene (MBBA) of formula:

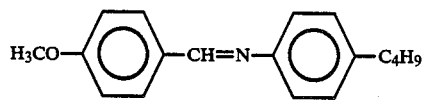
(XXV)

The aforementioned liquid crystals have the properties given in table 1 and certain of these properties can be improved by adding thereto one or more compounds of formula (I) according to the invention.

The present invention also relates to a process for preparing compounds in accordance with the aforementioned formula (I). This process consists of reacting an acid chloride of formula $R^1$—Z—COCL in which $R^1$ and Z have the meanings given hereinbefore with a compound according to formula:

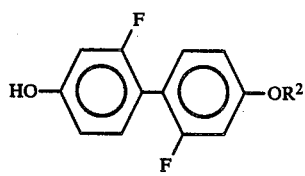
(II)

in which $R^2$ is a straight or branched alkyl radical with 1 to 12 carbon atoms.

This reaction can be performed at ambient temperature in an anhydrous solvent such as pyridine.

The acid chloride of formula $R^1$—Z—COCL can be prepared from the corresponding carboxylic acid of formula $R^1$—Z—COOH using conventional processes, e.g. by reacting the acid with the thionyl chloride.

When Z represents a single bond or a phenylene radical of formula

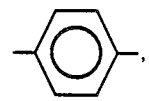

the corresponding carboxylic acids are generally commercially available or can be prepared by conventional methods.

When Z represents the bicyclo-(2,2,2)-octylene radical of formula

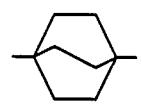

and $R^1$ represents an alkyl radical, it is possible to synthesize the corresponding acids using the method described by G. W. Gray and S. M. Kelly for the preparation of 1,4-disubstituted bicyclo-(2,2,2)-octanes (J. Chem. Soc. Perkin II, 1981, pp.26–31 and British Pat. No. 2069483). According to this method, one starts with the corresponding bromo derivatives of formula

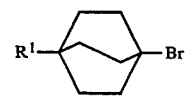

which can be obtained from $R^1$—$CH_2$—$COCH_3$ as is described in the aforementioned publications.

When Z represents the bicyclo-(2,2,2)-octylene radical and $R^1$ represents an alkoxy radical, it is possible to synthesize the corresponding acid by using the method described by W. Adcock and A. N. Abeywickrema in J. Org. Chem., 47, pp.2951–2957, 1982 for the preparation of the acid

When Z represents the cyclohexylene radical of formula

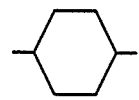

and $R^1$ represents an alkyl or alkoxy radical, it is possible to synthesize the corresponding acid by using the method described in Japanese patent 80/53244 of 18/4/80 (Chemical Abstract vol.93, 1980, no.167 736b).

When Z represents the radical derived from cubanite of formula:

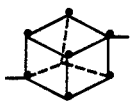

it is possible to synthesize the corresponding acid by using the methods described by Gray et al in Mol. Cryst. Liq. Cryst., 1983, vol.98, pp.425–431.

The invention also relates to 2,2'-difluoro-4-alkoxy-4'-hydroxydiphenyls of formula (II) which form the basic structure of the nematic liquid crystals according to the invention.

These compounds of formula (II) can be synthesized from 3-nitro-4-aminoanisole by a process corresponding to the following reaction diagram:

(b) condensing two molecules of 3-nitro-4-iodoanisole of formula (IV) to obtain 2,2'-dinitro-4,4'-dimethoxydiphenyl of formula (V), (c) reducing the $NO_2$ groups of the 2,2'-dinitro-4,4'-dimethoxydiphenyl of formula (V) into $NH_2$ groups to obtain the 2,2'-diamino-4,4'-dimethoxydiphenyl of formula (VI), (d) replacing the $NH_2$ groups of the 2,2'-diamino-4,4'-dimethoxydiphenyl of formula (VI) by fluorene atoms to obtain the 2,2'-difluoro-4,4'-dimethoxydiphenyl of formula (VII), (e) replacing the methoxy groups of the 2,2'-difluoro-4,4'-dimethoxydiphenyl of formula (VII) by hydroxyl groups to obtain the 2,2'-difluoro-4,4'-dihydroxydiphenyl of formula (VIII) and (f) reacting the 2,2'-difluoro-4,4'-dihydroxydiphenyl of formula (VIII) with a halogen derivative of formula

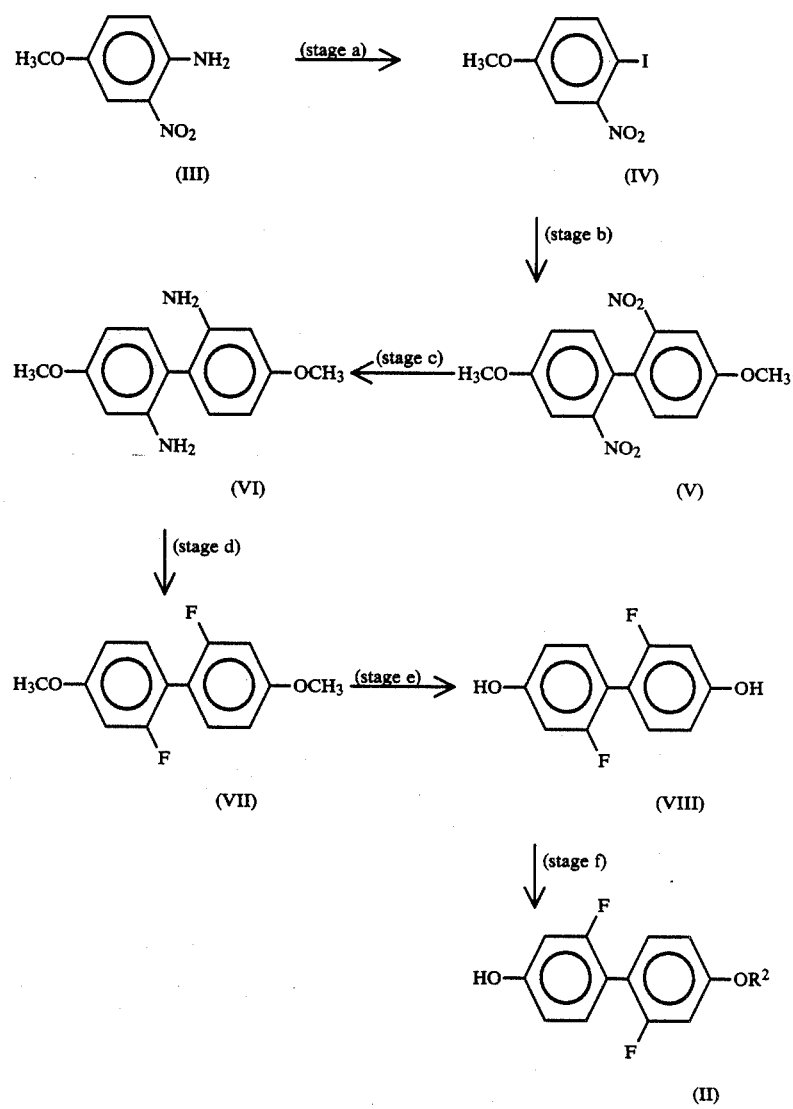

Thus, the process for the preparation of 2,2'-difluoro-4-alkoxy-4'-hydroxydiphenyls of formula (II) comprises the following stages:

(a) converting the 3-nitro-4-aminoanisole of formula (III) into 3-nitro-4-iodoanisole of formula (IV) by reacting with nitrous acid or an aqueous solution of alkali metal nitrite and alkali metal iodide, $R^2X$, in which X represents a halogen and $R^2$ represents an alkyl radical with 1 to 12 carbon atoms, to obtain the 2,2'-difluoro-4-alkoxy-4'-hydroxydiphenyl of formula (II).

The first stage (a) consisting of replacing the $NH_2$ substituent by an iodine atom can be performed according to the process described by H. Heaney and I. T. Millar in Organic Syntheses, vol.40, p.105 either by reacting the amino derivative with nitrous acid or an aqueous solution of alkali metal nitrite and alkali metal iodide. This reaction can be performed in concentrated hydrochloric acid by the dropwise addition to the solution of a sodium nitrite solution in water and then a sodium iodide solution.

The second stage (b) consising of condensing two molecules of 3-nitro-4-iodoanisole to form the 2,2'-dinitro-4,4'-dimethoxydiphenyl derivative can be performed by using the Ullmann condensation reaction described in Organic Syntheses, vol.3, p.339 and in J. Chem. Soc., p.2658, 1958. This reaction can be performed in an organic solvent, such as nitrobenzene using copper in powder form and heating to a temperature of 200° to 220° C.

The third stage (c) consisting of reducing the $NO_2$ groups of the compound of formula (V) into $NH_2$ group can be performed by conventional methods, e.g. by the action of hydrochloric acid in the presence of catalysts based on iron, zinc and tin, such as dihydrated tin (II) chloride.

The fourth stage (d) consisting of placing the $NH_2$ groups by fluorine atoms can be performed by using the Schiemann-Balz reaction described e.g. in Organic Reactions, vol.5, pp.193–228, 1949. According to this reaction, firstly a diazonium fluoroborate is obtained and the latter salt is then decomposed to obtain the corresponding fluorine derivative by liberating nitrogen and boron trifluoride. This reaction can be performed in concentrated hydrochloric acid by the action of nitrous acid or an aqueous solution of alkali metal nitrite and a solution of alkali metal tetrafluoroborate. Following the precipitation of the diazonium fluoroborate, the latter is separated from the solution, dried, slowly heated to an adequate temperature to decompose it and thus recover the difluorine derivative.

The fifth stage (e) consisting of replacing the methoxy groups by hydroxyl groups can be performed by using the reaction described by N. Carr, G. W. Gray and S. M. Kelly in Mol. Cryst. Liq. Cryst., 1985, vol.129, pp.301–313 for converting the methoxy phenyl bicyclo-(2,2,2)-octane derivative into hydroxyphenylbicyclo(2,2,2)-octane. This reaction can be performed by using hydrobromic acid and acetic acid in an aqueous medium, as is described in the above article.

The sixth stage (f) consisting of transforming one of the hydroxyl groups into an alkoxy group by reacting the compound of formula (VIII) with a halogen derivative of formula $R^2X$, in which X represents a halogen such as bromine and $R^2$ has the meaning given hereinbefore. At the end of the reaction, the monoether is separated from the diether by chromatography.

The thus prepared compounds of formula (II) are very useful for the synthesis of other compounds, because their structure constitutes a base for the production of numerous liquid crystals.

BRIEF DESCRIPTION OF THE DRAWING

The drawing shows a liquid crystal display device, partially in section, for use with compounds according to the invention.

DETAILED DESCRIPTION OF THE INVENTION RELATIVE TO THE DRAWING

Other features and advantages of the invention can be gathered from the following examples given in an illustrative and non-limitative manner relative to the attached drawing which, in vertical section, shows a liquid crystal display device using the compounds according to the invention.

EXAMPLE 1

Preparation of 2,2'-difluoro-4-ethoxy-4'-hydroxydiphenyl of formula:

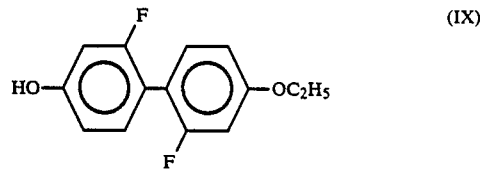

(a) preparation of 3-nitro-4-iodoanisole of formula (IV)

72.3 g of 3-nitro-4-aminoanisole are suspended in 210 ml of concentrated hydrochloric acid and the suspension is cooled to a temperature of 0° to 5° C., followed by the addition of 140 g of ice. This is followed by the dropwise addition of a solution of 32.2 g of sodium nitrite in 133 ml of water. The mixture is stirred for 15 minutes at 5° C., then filtered and the filtrate is poured on to a solution of 294 g of potassium iodide in 800 ml of water. The precipitate obtained is filtered, washed successively with water, with a 5% sodium sulphite solution in water and then with water again and is dried in vacuo. The crude product is purified by vacuum distillation, thus giving 90 g of the compound of formula (IV), which corresponds to a yield of 75%. The boiling point of the compound is 173° C. under 0.9 mm Hg and its melting point is 61° C.

(b) preparation of 2,2'-dinitro-4,4'-dimethoxydiphenyl of formula (V)

A solution of 50 g of 3-nitro-4-iodoanisole obtained in (a) are heated to 190° C. in 50 ml of nitrobenzene and 45 g of copper powder are added thereto over a period of 15 minutes. The mixture is vigorously stirred and heated for a further 30 minutes at 200° to 210° C. The mixture is left to cool and toluene is added thereto. The solution is filtered and the solvent is distilled, i.e. the toluene and nitrobenzene. This gives a brown solid product which is purified by successive recrystallizations in methanol, which gives 16.5 g of bright yellow needles of the compound of formula (V). Its melting point is 132° C. and the yield is 60%.

(c) preparation of 2,2'-diamino-4,4'-dimethoxydiphenyl of formula (VI)

10 g of 2,2'-dinitro-4,4'-dimethoxydiphenyl previously obtained with 74.2 g of dihydrated tin (II) chloride are suspended in 130 ml of ethanol. The solution is vigorously stirred and 20 ml of concentrated hydrochloric acid are added dropwise thereto whilst regulating the hydrochloric acid addition speed in such a way as to not too violently heat the reaction medium. After 20 minutes, a clear homogeneous solution is obtained. Stirring takes place for a further 2 hours, followed by cooling the solution with ice and is followed by the slow pouring of a 2 mol./$1^{-1}$ concentrated soda solution. Thus, the tin (IV) tetrachloride and the 2,2'-diamino-4,4'-dimethoxydiphenyl are precipitated. Further soda is added to adjust the pH-value of the solution to a basic level of approximately 14. This leads to the disappearance of the mineral precipitate and it is possible to filter the 2,2'-diamino-4,4'-dimethoxydiphenyl. The precipitate is washed several times with water, is then taken up in ethyl ether, filtered and dried on sodium sulphate. The product obtained is then purified by recrystallization in ethanol, which gives 6.85 g of the compound of formula (VI). The melting point is 108°–109° C. and the yield 85%.

(d) preparation of 2,2'-difluoro-4,4'-dimethoxydiphenyl of formula (VII)

6.8 g of the compound obtained in stage (c) are suspended in 8 ml of concentrated hydrochloric acid, followed by the addition of 8 ml of dioxan. This is followed by the dropwise addition of a solution of 4.5 g of sodium nitrite in 12 ml of water at a temperature of 0° C. Immediately thereafter and still at 0° C., a solution of 13.4 g of sodium tetrafluoroborate in 30 ml of water is added. 30 minutes after the addition of the fluorine reagent has ended, the precipitate formed is filtered, washed with ice wate and then dried in vacuo at ambient temperature. The dried powder is suspended in 200 ml of anhydrous xylene and then the mixture is slowly refluxed. At approximately 110° C., the emission of white $BF_3$ smoke starts and the reaction is stopped when the gaseous emission ends. The mixture is filtered and then the xylene is eliminated by distilling under atmospheric pressure. The residue obtained is then dissolved hot in ethanol and is recrystallized, which gives 3 g of 2,2'-difluoro-4,4'-dimethoxydiphenyl of formula (VII) with a melting point of 70° C. and a yield of 43%.

(e) preparation of 2,2'-difluoro-4,4'-dihydroxydiphenyl of formula (VIII)

3 g of the compound obtained in stage (d) are dissolved in 25 ml of an aqueous 48 to 50% hydrobromic acid solution and 83 ml of a hydrobromic acid solution in 45% acetic acid and refluxing takes place for 20 hours. The cooled solution is then added to 100 ml of water, followed by stirring with ethyl ether. The organic phase is washed with a 10% sodium carbonate solution and then with water, followed by drying on sodium sulphate. The product obtained is recrystallized in chloroform and in this way 1.7 g of 2,2'-difluoro-4,4'-dihyroxydiphenyl of formula (VIII) is obtained with a melting point above 210° C. (sublimation) and a yield of 64%.

(f) preparation of 2,2'-difluoro-4-ethoxy-4'-hydroxydiphenyl of formula (IX)

1 g of the compound of formula (VIII) obtained in stage (e) is dissolved in 250 ml of anhydrous methylethyl ketone, followed by the addition of 4 g of potassium carbonate and vigorous stirring. This is followed by the dropwise addition of a solution of 0.5 g of bromoethane in 10 ml of methylethyl ketone. The mixture is refluxed for 20 hours and then the solution is poured on to 400 ml of ice water, followed by extraction with chloroform. The organic phase is washed with water and dried on sodium sulphate. The residue obtained undergoes chromatography on a silica column by eluting with a chloroform—diethyl ether mixture (95:5 by volume). Thus, firstly the 2,2'-difluoro-4,4'-diethoxydiphenyl is recovered, followed by 0.45 g of 2,2'-difluoro-4-ethoxy-4'-hydroxydiphenyl of formula (IX), which has a melting point of 106.5° C. and with a yield of 40%.

EXAMPLE 2

Preparation of other compounds according to formula (II):

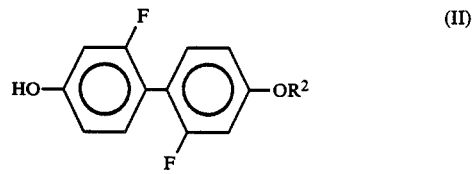

The same operating procedure as in example 1 is used for preparing the compounds of the following table 2. The melting point of these compounds is also given in table 2.

In the case of the compound of formula (II) having the 2-(methylbutyloxy)-4-hydroxy-4'-diphenyl radical of formula:

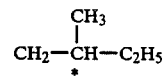

the operating procedure of example 1 is again followed, but in stage (f) the reagent used is (S) 1-bromo-2-methylbutane previously synthesized from (S) 2-methyl-1-butanol by the method described by G. W. Gray and D. G. McDonnel (Mol. Cryst. Liq. Cryst., 1976, vol. 37, pp. 189–211).

EXAMPLE 3

Preparation of 2,2'-difluoro-4-ethoxy-para-n-butoxy-4'-diphenyl benzoate of formula:

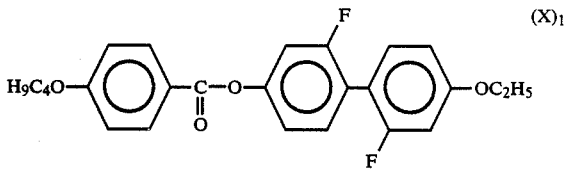

designed hereinafter by PF402.

(1) preparation of the para-n-butoxy benzoic acid chloride

A solution of 5 g of para-n-butoxy benzoic acid is refluxed for 2 hours in 8 ml of thionyl chloride. The thionyl chloride is then distilled, followed by distillation under reduced pressure and under a dry nitrogen stream of the expected acid chloride. In this way para-n-butoxy benzoic acid chloride of the following formula is obtained:

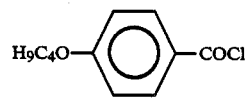

(2) preparation of 2,2'-difluoro-4-para-n-butoxy-diphenyl-4'-benzoate of formula (X)

0.4 g of 2,2'-difluoro-4-ethoxy-4'-hydroxydiphenyl obtained in example 1 is dissolved in 20 ml of anhydrous pyrridine. 0.41 g of the previously obtained acid chloride is added dropwise to the vigorously stirred solution. The mixture is stirred at ambient temperature for 24 hours and then poured on to 50 ml of iced 10% hydrochloric acid solution. The precipitate obtained is filtered, washed with a 10% hydrochloric acid solution to eliminate all the pyrridine and then with water until neutral wash waters are obtained. The product is taken up by chloroform and dried on sodium sulphate. The crude product undergoes chromatography on a silica column, followed by eluting with chloroform and recrystallization in methanol. This gives 0.54 g of 2,2'-difluoro-4-ethoxy-para-n-butoxy-diphenyl-4'-benzoate which corresponds to an 80% yield.

This product is mesogenic and has a wide nematic range between the temperature of passing from the solid state to the nematic state $T_{KN}$ and the temperature for passing from the nematic state to the isotropic state $T_{NI}$, $T_{KN}$ being 124° C. and $T_{NI}$ 193° C.

2,2'-difluoro ((S) 2-methylbutyloxy)-4-para-n-decyloxydiphenyl-4'-benzoate is prepared in the same way.

The characteristics of the two compounds obtained in example 3 are given in table 3.

EXAMPLE 4

Preparation of 2,2'-difluoro-4-ethoxy-para-n-pentyl-diphenyl-4'-transcyclohexanoate of formula:

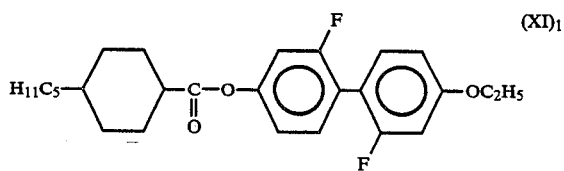

designated hereinafter by CHF52.

(1) preparation of the para-n-pentyl-transcyclohexanoic acid chloride

A solution of 5 g of para-n-pentyl-transcyclohexanoic acid is refluxed in 8 ml of thionyl chloride for 2 hours. The thionyl chloride is then eliminated by distilling under atmospheric pressure. The acid chloride is then distilled under reduced pressure and under a dry nitrogen stream. This gives a product with a boiling point of 87° C. under 0.5 mm Hg.

(2) preparation of 2,2'-difluoro-4-para-n-pentyl-diphenyl-4'-tanscyclohexanoate of formula (XI)

0.3 g of 2,2'-difluoro-4-ethoxy-4'-hydroxydiphenyl obtained in example 1 is dissolved in 15 ml of anhydrous pyrridine. 0.3 g of the acid chloride previously obtained is then added dropwise to this solution. The mixture is stirred for 24 hours at ambient temperature, followed by pouring on to 50 ml of a 10% hydrochloric acid solution. The precipitate obtained is filtered and washed with 10% hydrochloric acid and then with water. The product is taken up with chloroform and dried on sodium sulphate. The crude mixture obtained undergoes chromatography on a silica column whilst carrying out elution by means of chloroform, followed by recrystallization thereof in methanol. This gives 0.4 g of 2,2'-difluoro-4-ethoxy-para-n-pentyl-diphenyl-4'-transcyclohexanoate, which corresponds to a yield of 79%.

This product is mesogenic and has a wide nematic range, because $T_{KN}$ is 74° C. and $T_{NI}$ 170° C.

EXAMPLE 5

The compounds of formula:

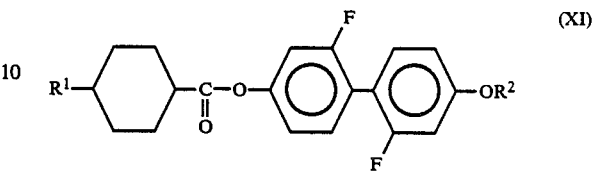

of the attached table 4 are prepared as in Example 4. The characteristics of the compounds obtained are also given in Table 4.

EXAMPLE 6

Preparation of 2,2'-difluoro-4-para-n-hexyl-diphenyl-4'-benzoate of formula:

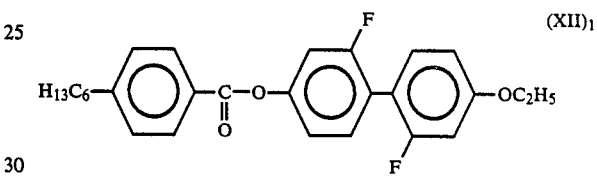

designated hereinafter by PF62.

(1) preparation of para-n-hexyl benzoic acid chloride

A solution of 3 g of para-n-hexyl benzoic acid is refluxed in 7 ml of thionyl chloride for 2 hours. The thionyl chloride is eliminated by distillation under atmospheric pressure, followed by the distillation of the acid chloride under reduced pressure and under a dry nitrogen stream. This gives a product with a boiling point of 153° C. under 1.2 mm Hg.

(2) preparation of the 2,2'-difluoro-4-ethoxy-para-n-hexyldiphenyl-4'-benzoate of formula (XII)

0.3 g of the 2,2'-difluoro-4-ethoxy-4'-hydroxy diphenyl obtained in example 1 is dissolved in 15 ml of anhydrous pyrridine. 0.32 g of the previously obtained acid chloride is then added dropwise to this solution. The mixture is stirred for 24 hours at ambient temperature and then poured on to 50 ml of a 10% hydrochloric acid solution. The precipitate obtained is filtered and washed with 10% hydrochloric acid and then with water. The product is taken up with chloroform and dried on sodium sulphate. The crude product obtained undergoes chromatography on a silica column, whilst carrying out elution by means of chloroform and this is followed by recrystallization thereof in methanol. This gives 0.42 g of 2,2'-difluoro-4-ethoxy-para-n-hexyl-diphenyl-4'-benzoate corresponding on an 80% yield. This product is mesogenic and has a wide nematic range, because $T_{KN}$ is 74.4° C. and $T_{NI}$ 142.5° C.

EXAMPLE 7

The compounds of formula:

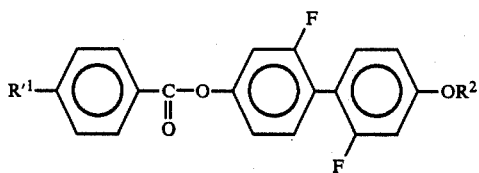

referred to in table 5 are prepared as in example 6, whilst using the operating procedure of the latter. The characteristics of the products obtained are also given in table 5.

EXAMPLE 8

Preparation of 2,2'-difluoro-4-ethoxy-4'-(n-pentyl bicyclo(2,2,2)-octanoate)-diphenyl of formula:

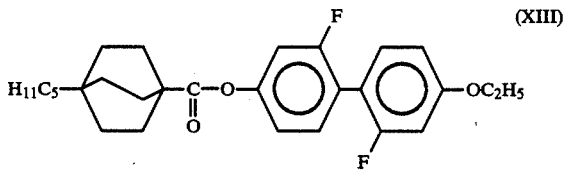

designated hereinafter by BCOF52.

(1) preparation of the n-pentyl-1-bicyclo(2,2,2)-4-octanoic acid chloride n-pentyl-4-bicyclo-(2,2,2)-octanoic acid is obtained by the methods described in the literature and quoted hereinbefore (p.8) (melting point 160° C.). A solution of 1 g of said acid in 4 ml of thionyl chloride is refluxed for 2 hours. The thionyl chloride is eliminated by distillation under atmospheric pressure. The acid chloride obtained is used as such and without further purification.

(2) preparation of the 2,2'-difluoro-4-ethoxy-4'-(n-pentyl-4-bicyclo(2,2,2)-1-octanoate)-diphenyl of formula (XIII)

0.3 g of the 2,2'-difluoro-4-ethoxy-4'-hydroxydiphenyl obtained in example 1 is dissolved in 15 ml of anhydrous pyrridine. 0.35 g of the previously obtained acid chloride is added dropwise to this solution. The mixture is stirred for 24 hours at ambient temperature and then poured on to 50 ml of a 10% hydrochloric acid solution. The precipitate obtained is filtered and washed with 10% hydrochloric acid and then with water. The product is taken up by chloroform and dried on sodium sulphate. The crude product obtained undergoes chromatography on a silica column, whilst carrying out elution by means of chloroform. This is followed by the recrystallization thereof in methanol. 0.41 g of 2,2'-difluoro-4-ethoxy-4'-(n-pentyl-4-bicyclo-(2,2,2)-octanoic)diphenyl is obtained, which corresponds to a yield of 76%. This product is mesogenic and has a wide nematic range, because $T_{KN}$ is 102° C. and $T_{NI}$ 205.5° C.

The 2,2'-difluoro-4-alkoxy-4'-hydroxydiphenyl derivatives are in accordance with formula (I), particularly those of examples 2 to 5 can be used as liquid crystals in the display device shown in vertical section in the attached drawing. In the latter it is possible to see that the display device comprises two insulating, transparent walls 1, 3 and sealing joints 5, 7 define an inner cavity 8 filled with liquid crystal. The two insulating walls are internally coated with a system of crossbar electrodes 9, 11 making it possible to determine the display zones. A system of crossed polarizers 13, 15 is located on either side of walls 1, 3 and a control system 17 makes it possible to apply a voltage to the desired electrodes. During operation, to certain of the electrodes are applied the desired voltages for deforming the liquid crystal in the zones corresponding to these electrodes and thus obtain a display.

This electrode control device can be of the type described in European Pat. No. 0055966 of the Commissariat à l'Energie Atomique. In this device, the liquid crystal used can be constituted by compounds of formula (I) of the invention, particularly in the form of mixtures of these compounds or mixtures of these compounds with other liquid crystals. The following examples illustrate the production of such mixtures.

EXAMPLE 9

A mixture of 21% by weight of PF65 of table 5, 16.5% by weight of PF64 of table 5, 22% by weight of CHF44 of table 4, 19.5% by weight of CHF43 of table 4, 21% by weight of CHF33 of table 4 is formed. This gives a mixture of liquid crystals having a nematic mesomorphic phase in the temperature range from $-10°$ C. to $+138.2°$ C.

The dielectric anisotropy $\Delta\epsilon$, the optical anisotropy $\Delta n$ and the $K_{33}/K_{11}$ ratio of the mixture obtained are measured and the following values obtained:
$\Delta n = 0.1744$ at 633 nm and at 20° C.
$\Delta\epsilon = -2.7$
$K_{33}/K_{11} = 1.76$ at 20° C.

EXAMPLE 10

A mixture of liquid crystals comprising 53.7% by weight of I22 of formula (XVIII), 18.7% by weight of CHF33 of table 4, 13.00% by weight of CHF43 of table 4 and 14.6% by weight of CHF44 of table 4 is prepared. This gives a mixture of liquid crystals having a nematic mesomorphic phase in the temperature range from $<-10°$ C. to 102.5° C. The optical anisotropy $\Delta n$, the $K_{33}/K_{11}$ ratio and the dielectric anisotropy are measured and the following values obtained:
$\Delta n = 0.152$ at 20° C. (633 nm)
$\Delta\epsilon = -1.0$
$K_{33}/K_{11} = 1.62$ at 20° C.

EXAMPLE 11

A mixture of liquid crystals comprising 54.1% by weight of MBBA of formula (XXV), 26.1% by weight of CHF33 of table 4 and 19.8% by weight of CHF43 of Table 4 is prepared. This mixture has a mesomorphism range of $-3°$ C. to 93° C., an optical anisotropy $\Delta n$ of 0.18, a dielectric anisotropy $\Delta\epsilon$ of $-1.2$ and constant elastic $K_{33}/K_{11}$ ratio of $>1.4$.

EXAMPLE 12

A mixture of liquid crystals comprising 38.8% by weight of I22 of formula (XVIII), 26.9% by weight of MBBA of formula (XXV), 14.4% by weight of CHF33 of table 4, 9.7% by weight of CHF43 of Table 4 and 10.2% by weight of CHF44 of table 4 is prepared. This mixture has a mesomorphism range of $-24°$ C. to 87° C., an optical anisotropy $\Delta n$ of 0.16, a dielectric anisotropy $\Delta\epsilon$ of $-0.85$ and a constant elastic $K_{33}/K_{11}$ ratio of $>1.4$.

EXAMPLE 13

A mixture of liquid crystals comprising 47.7% by weight of BCH52FF of formula (XXIV), 20.8% by weight of CHF33 of table 4, 16.5% by weight of CHF44 of table 4 and 15.0% by weight of CHF43 of table 4 is prepared. The mixture has a mesomorphism range of $<-10°$ to 117° C., an optical anisotropy $\Delta N$ of 0.13, a dielectric anisotropy $\Delta\epsilon$ of $-1.3$ and a constant elastic $K_{33}/K_{11}$ ratio of $>1.4$.

EXAMPLE 14

A liquid crystal mixture comprising 19.5% by weight of BCO55F of formula (XXII), 45.4% by weight of I22 of formula (XVIII), 5.6% by weight of CHF52 of table 4, 16.9% by weight of CHF33 of table 4 and 12.6% by weight of CHF44 of table 4 is prepared. The mixture has a mesomorphism range of $<-10°$ to 95° C., an optical anisotropy $\Delta n$ of 0.112, a dielectric anisotropy $\Delta\epsilon$ of $-0.9$ and a constant elastic $K_{33}/K_{11}$ ratio of $>1.4$.

TABLE 2

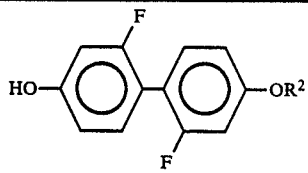
(II)

| Compound of formula (II) | $R^2$ | Melting Point $T_f$ |
|---|---|---|
| 2,2'-difluoro-4-ethoxy-4'-hydroxydiphenyl | $C_2H_5$ | 106.5° C. |
| 2,2'-difluoro-4-n-propyloxy-4'-hydroxydiphenyl | $C_3H_7$ | 93.7° C. |
| 2,2'-difluoro-4-n-butyloxy-4'-hydroxydiphenyl | $C_4H_9$ | 103.8° C. |
| 2,2'-difluoro-4-n-pentyloxy-4'-hydroxydiphenyl | $C_5H_{11}$ | 107° C. |
| 2,2'-difluoro-4-(2-methylbutyl oxy)-4'-hydroxydiphenyl | $CH_3$ $\mid$ $CH_2-CH-C_2H_5$ $*$ | 113° C. |

TABLE 1

| Liquid crystal | Nematic mesomorphism range | Optical anisotropy $\Delta n$ | Dielectric anisotropy $\Delta\epsilon$ | $K_{33}/K_{11}$ |
|---|---|---|---|---|
| 1-(alkylcyclohexyl) 2-(alkylfluorobiphenyl)-ethane I22 | $-10$ to 102° C. | 0.149 | $-0.05$ | 1.2 |
| alkylfluorophenyl-alkylbicyclooctane carboxylates BCO55F | 26.3 to 64° C. | 0.06 | $-0.72$ | 1.35 |
| p-methoxy-benzylidene p'-butylaniline MBBA | 18° to 42° C. | 0.17 | $-0.4$ | 1.32 |
| cyclonexhyldiphenyl BCH52FF | 27° C. to 78° C. | 0.099 | $-0.47$ | 1.76 |

TABLE 3

Compound of formula:

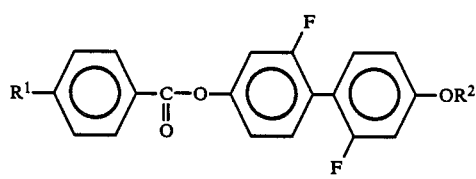
(X)

| Compound of formula (X) | Designation | $R^1$ | $R^2$ | $T_{KN}$ | $T_{NI}$ |
|---|---|---|---|---|---|
| 2,2'-difluoro-4-ethoxy-para-n-butoxy-4'-diphenyl benzoate | PF402 | $OC_4H_9$ | $C_2H_5$ | 124° C. | 193° C. |
| 2,2'-difluoro ((S) 2-methyl butyloxy)-4-para-n-decyloxy-4'-diphenyl benzoate | | $OC_{10}H_{21}$ | $CH_3$ $\mid$ $CH_2-CH-C_2H_5$ $*$ | 71° C. | 109.9° C |

TABLE 4

Compound of formula:

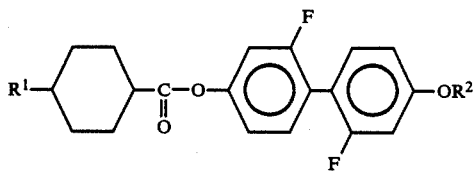
(XI)

| Compound of formula (XI) | Designation | $R^1$ | $R^2$ | $T_{KN}$ | $T_{NI}$ |
|---|---|---|---|---|---|
| 2,2'-difluoro-4-ethoxy-para-n-pentyl-diphenyl-4'-transcyclohexanoate | CHF52 | $C_5H_{11}$ | $C_2H_5$ | 74° C. | 170° C. |
| 2,2'-difluoro-4-n-propyloxy-para-n-pentyl-diphenyl-4'-transcyclohexanoate | CHF53 | $C_5H_{11}$ | $C_3H_7$ | 66° C. | 156.7° C. |
| 2,2'-difluoro-4-n-butyloxy-para-n-pentyl-diphenyl-4'-transcyclohexanoate | CHF54 | $C_5H_{11}$ | $C_4H_9$ | 65.4° C. | 154.9° C. |
| 2,2'-difluoro-4-n-propyloxy-para-n-butyl-diphenyl-4'-transcyclohexanoate | CHF43 | $C_4H_9$ | $C_3H_7$ | 61.6° C. | 152.4° C. |
| 2,2'-difluoro-4-n-butyloxy-para-n-butyl-diphenyl-4'-transcyclohexanoate | CHF44 | $C_4H_9$ | $C_4H_9$ | 51.3° C. | 149.3° C. |
| 2,2'-difluoro-4-n-propyloxy-para-n-propyl-diphenyl-4'-transcyclohexanoate | CHF33 | $C_3H_7$ | $C_3H_7$ | 56.7° C. | 158.1° C. |
| 2,2'-difluoro-4-n-butyloxy-para-n-butyl-diphenyl-4'-transcyclohexanoate | CHF34 | $C_3H_7$ | $C_4H_9$ | 41.1° C. | 157.1° C. |
| 2,2'-difluoro ((S) methyl) 2-butyloxy)-4-para-n-butyl-4'-diphenyl-transcyclohexanoate | CHF45* | $C_4H_9$ | $CH_2-\overset{*}{C}H(CH_3)-C_2H_5$ | 35.8° C. | 99.8° C. |

TABLE 5

Compound of formula:

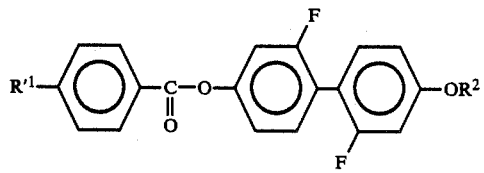
(XII)

| Compound of formula (XII) | Designation | $R'^1$ | $R^2$ | $T_{KN}$ | $T_{NI}$ |
|---|---|---|---|---|---|
| 2,2'-difluoro-4-ethoxy-para-n-hexyl-diphenyl-4'-benzoate | PF62 | $C_6H_{13}$ | $C_2H_5$ | 74.4° C. | 142.5° C. |
| 2,2'-difluoro-4-n-propyloxy-para-n-hexyl-diphenyl-4'-benzoate | PF63 | $C_6H_{13}$ | $C_3H_7$ | 74° C. | 127° C. |
| 2,2'-difluoro-4-n-butyloxy-para-n-hexyl-diphenyl-4'-benzoate | PF64 | $C_6H_{13}$ | $C_4H_9$ | 55° C. | 131° C. |
| 2,2'-difluoro-4-n-pentyloxy-para-n-hexyl-diphenyl-4'-benzoate | PF65 | $C_6H_{13}$ | $C_5H_{11}$ | 55° C. | 123° C. |
| 2,2'-difluoro ((S) methyl-2 butyloxy)-4-para-n-octyl-diphenyl-4'-benzoate | PF85* | $C_8H_{17}$ | $CH_2-\overset{*}{C}H(CH_3)-C_2H_5$ | 54.8° C. | 81.3° C. |

What is claimed is:

1. A 2,2'-difluoro-4-alkoxy-4'-hydroxydiphenyl derivative according to formula:

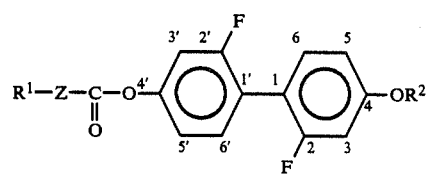
(I)

in which $R^1$ represents a straight or branched alkoxy or alkyl radical with 1 to 12 carbon atoms, Z represents a radical chosen from among:

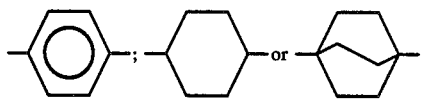

and $R^2$ represents a straight or branched alkyl radical with 1 to 12 carbon atoms.

2. A 2,2'-difluoro-4-alkoxy-4'-hydroxydiphenyl derivative according to claim 1, wherein it is in accordance with formula:

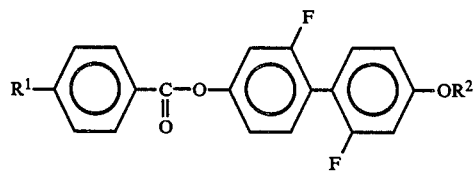

(X)

in which $R^1$ is the butyloxy radical and $R^2$ the ethyl radical, or in which $R^1$ is the decyloxy radical and $R^2$ and 2-methylbutyl radical (S).

3. A 2,2'-difluoro-4-alkoxy-4'-hydroxydiphenyl derivative according to claim 1, wherein it is in accordance with the formula:

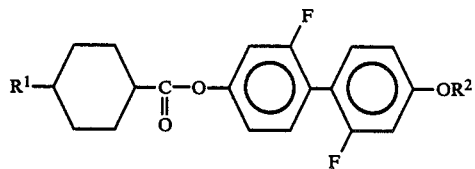

(XI)

in which $R^1$ is an alkyl radical with 3 to 5 carbon atoms and $R^2$ an alkyl radical with 2 to 5 carbon atoms.

4. A 2,2'-difluoro-4-alkoxy-4'-hydroxydiphenyl derivative according to claim 1, wherein it complies with the formula:

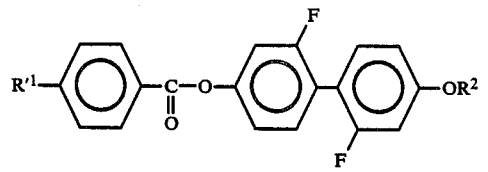

(XII)

in which $R^1$ is an alkyl radical with 6 to 8 carbon atoms and $R^2$ an alkyl radical with 2 to 5 carbon atoms.

5. A 2,2'-difluoro-4-alkoxy-4'-hydroxydiphenyl derivative according to claim 1, wherein it complies with the formula:

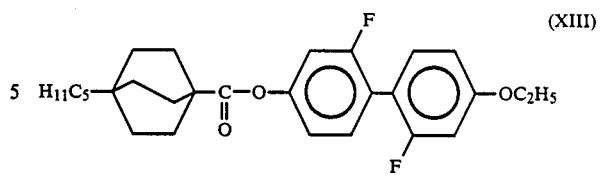

(XIII)

6. A mixture of liquid crystals comprising at least one 2,2'-difluoro-4-alkoxy-4'-diphenyl derivative according to one of the claims 1 to 5 and at least one compound chosen from among:

(a) the Schiff bases complying with formula:

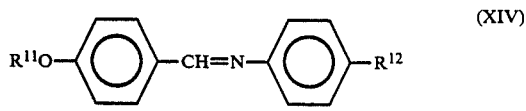

(XIV)

in which $R^{11}$ and $R^{12}$, which can be the same or different, are alkyl radicals with 1 to 7 carbon atoms, (b) 1-(alkylcyclohexyl)-2-(alkylfluorodiphenylyl)-ethane of formula:

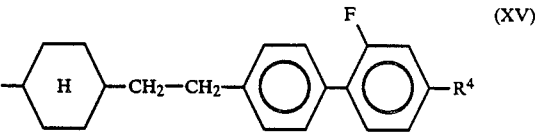

(XV)

in which $R^3$ and $R^4$, which can be the same or different, are alkyl radicals with 1 to 7 carbon atoms and (c) the alkylfluorophenyl-alkylbicyclooctane carboxylates of formula:

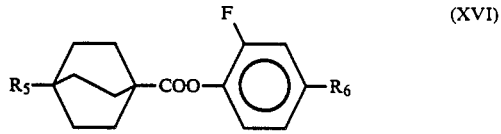

(XVI)

in which $R_5$ and $R_6$, which can be the same or different, are alkyl radicals with 1 to 7 carbon atoms, (d) the cyclohexyl diphenyl of formula:

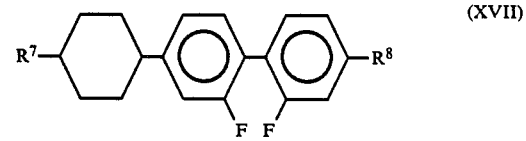

(XVII)

in which $R_7$ is an alkyl radical with 1 to 12 carbon atoms and $R_8$ an alkyl or alkoxy radical with 1 to 12 carbon atoms.

7. A mixture of liquid crystals according to claim 6, wherein the content of the mixture in compounds of formula (I) represents at least 10% by weight of the mixture.

8. A liquid crystal display device using the electrically controlled birefringence effect, wherein the liquid crystal comprises at least one 2,2'-difluoro-4-alkoxy-4'-hydroxydiphenyl derivative according to claim 1.

* * * * *